(12) United States Patent
Lewander Xu et al.

(10) Patent No.: US 9,841,374 B2
(45) Date of Patent: Dec. 12, 2017

(54) SYSTEM AND METHOD FOR DETERMINING A CONCENTRATION OF A GAS IN A CONTAINER

(71) Applicant: GasPorOx AB, Lund (SE)

(72) Inventors: Märta Lewander Xu, Lund (SE); Johannes Swartling, Lund (SE); Daniel Karlsson, Lund (SE); Patrik Lundin, Södra Sandby (SE); Joan Sandberg, Malmö (SE)

(73) Assignee: GasPorOx AB, Lund (SE)

( * ) Notice: Subject to any disclaimer, the term of this patent is extended or adjusted under 35 U.S.C. 154(b) by 0 days.

(21) Appl. No.: 14/891,956

(22) PCT Filed: May 27, 2014

(86) PCT No.: PCT/EP2014/061001
§ 371 (c)(1),
(2) Date: Nov. 17, 2015

(87) PCT Pub. No.: WO2014/191438
PCT Pub. Date: Dec. 4, 2014

(65) Prior Publication Data
US 2016/0169796 A1    Jun. 16, 2016

(30) Foreign Application Priority Data

May 27, 2013 (SE) ........................................ 1350640
May 27, 2013 (SE) ........................................ 1350641

(51) Int. Cl.
*G01N 21/03* (2006.01)
*G01N 21/00* (2006.01)
(Continued)

(52) U.S. Cl.
CPC ......... *G01N 21/39* (2013.01); *G01N 21/0303* (2013.01); *G01N 21/61* (2013.01);
(Continued)

(58) Field of Classification Search
USPC .................................................. 356/432–444
See application file for complete search history.

(56) References Cited

U.S. PATENT DOCUMENTS 3,614,243 A * 10/1971 Harvey .............. G01N 21/0303
250/429
5,026,991 A * 6/1991 Goldstein .............. G01N 21/39
250/339.04
(Continued)

FOREIGN PATENT DOCUMENTS

JP    2009-14589 A    1/2009

OTHER PUBLICATIONS

WIPO, European International Search Authority, International Search Report and Written Opinion dated Jul. 17, 2014 in International Patent Application No. PCT/EP2014/061001, 10 pages.

*Primary Examiner* — Tri Ton
*Assistant Examiner* — Jarreas C Underwood
(74) *Attorney, Agent, or Firm* — Inskeep IP Group, Inc.

(57) ABSTRACT

A system and method for measuring a concentration of a gas in a container having at least one flexible or variable side or wall. The system and method comprising creating a determinable optical path length through the container having a shape. Positioning a light source head and a detector head against at least one of the least one flexible or variable side or wall. Transmitting a light signal between the light source head and the detector head through the determinable optical path length. Determining the concentration of the gas in the container based on detected light and the determinable optical path length.

19 Claims, 14 Drawing Sheets

(51) Int. Cl.
*G01N 21/39* (2006.01)
*G01N 21/61* (2006.01)
*G01N 21/27* (2006.01)

(52) U.S. Cl.
CPC ... *G01N 21/274* (2013.01); *G01N 2021/0364* (2013.01); *G01N 2201/066* (2013.01); *G01N 2201/06113* (2013.01)

(56) References Cited

U.S. PATENT DOCUMENTS

| | | | | |
|---|---|---|---|---|
| 5,317,156 | A * | 5/1994 | Cooper | G01N 21/39 250/339.13 |
| 7,471,393 | B2 * | 12/2008 | Trainer | G01N 15/0205 356/336 |
| 8,379,209 | B2 * | 2/2013 | Yokobayashi | G01N 21/3504 356/437 |
| 2008/0221711 | A1 * | 9/2008 | Trainer | G01N 15/0205 700/54 |
| 2009/0059332 | A1 * | 3/2009 | DiFoggio | G01N 21/0303 359/196.1 |
| 2012/0140229 | A1 * | 6/2012 | Svanberg | G01N 21/1702 356/437 |

* cited by examiner

SYSTEM AND METHOD FOR DETERMINING A CONCENTRATION OF A GAS IN A CONTAINER

RELATED APPLICATIONS

This application is the U.S. National Phase of and claims priority to International Patent Application No. PCT/EP2014/061001, International Filing Date May 27, 2014, entitled System And Method For Determining A Concentration Of A Gas In A Container; which claims benefit of Swedish Application No. SE13506415 filed May 27, 2013 entitled System And Method For Determining A Concentration Of A Gas In A Container; and Swedish Application No. SE13506407 filed May 27, 2013 entitled System And Method For Determining A Concentration Of A Gas In A Container; all of which are incorporated herein by reference in their entireties.

BACKGROUND OF THE INVENTION

Field of the Invention

This disclosure pertains in general to determine a concentration of gaseous content in a container with non-well defined outer geometry. More particularly the disclosure relates to gas absorption spectroscopy of gaseous content in a container. Especially the disclosure relates to determining or calibrate for an optical path length in containers with at least one flexible or variable wall which is optically transparent or translucent.

Background of the Disclosure

Optical absorption spectroscopy is an established method to measure gaseous species inside containers, in a non-invasive and non-destructive manner. In traditional analysis, the procedure requires that the optical path length in the volume containing the gaseous species to be measured is well defined, which can be accomplished e.g. by using special purpose containers (vials) with optical grade transparent walls and known distance between the walls. However, there is a great need in certain applications to be able to monitor or quantify the gases inside containers that have not been designed for the purpose of spectroscopic measurements. Examples of such applications include packages of foodstuffs that utilize modified atmosphere packaging (MAP) to prolong or ensure longevity. Such packages are normally not designed with spectroscopic analysis in mind and may be made of flexible or soft materials. It is desired to measure the gaseous content of such containers for the purposes of process control and quality control. Similar applications exist in the areas of packaging of pharmaceuticals and other medical products. Such measurements may be carried out either manually or in an automated manner in a production or transport logistics line.

Hence, new improved apparatus and methods for determining an optical path length in such containers would be advantageous.

SUMMARY OF THE INVENTION

Accordingly, examples of the present disclosure preferably seek to mitigate, alleviate or eliminate one or more deficiencies, disadvantages or issues in the art, such as the above-identified, singly or in any combination by providing a device, system or method according to the appended patent claims for determining an optical path length in containers with flexible or variable and optically transparent or translucent walls.

Herein a container may be either a container having at least one flexible wall or a container with an unpredictable path length due to, for example, the content. Examples of such containers but not limited to are, flexible bags, e.g. bags made of plastic, or a tray with, for example, a covering cling films or plastic wrap, trays made of semi-rigid or rigid plastic used for food stuff.

In a first aspect a method of determining a concentration of a gas in a container having at least one flexible or variable side or wall is disclosed. The method comprising creating a determinable optical path length through said container having a shape.

Some technique disclosed herein for creating a determinable optical path length pertains to modify the shape of the flexible or semi-rigid container. By modify the shape of the container, a fixed optical path length may be provided between two points. The optical path length may then be established either from the fixed distance obtained between the walls of the modified container or indirectly as part of determining the concentration of the gaseous content using a calibration routine.

Absorption signals are recorded or obtained by transmitting a light signal between a light source head and a detector head through the determinable optical path length. Determining the concentration of gas in the container based on detected light and the determinable optical path length.

The absorption signal may be a full absorption spectrum or a signal from at least one discrete wavelength.

In some examples of the disclosure, the method comprises modifying the shape of the container for the creating the determinable optical path length through the container having a shape.

Some examples of the disclosure, further comprises positioning a light source head and a detector head against at least one of the least one flexible or variable side or wall.

Positioning the light head and detector head may be done simultaneously as the shape of the container is modified or subsequent to the modification of the shape.

After the shape has been modified a fixed and determinable optical path length is obtained between at least two walls or sides of the container. The optical path length may then be established. Alternatively, since the optical path length for the same type of container may be repeatable fixed the same distance, the measurement conditions are traceable. Hence, instead of directly determining the optical path length through the container, a calibration routine may be performed. The calibration routine may include measuring one or more similar containers with a known concentration of the gas and where the optical path length has been created and fixed to the same distance as the optical path length of the container with an unknown concentration of the gas.

In some examples of the disclosure, the modifying the shape of the container includes pulling at least one side or wall a distance relative at least one second side or wall by using at least one movable temporary attachment point, such as at least two movable temporary attachment points, thereby creating the determinable optical path length through the container.

In some examples of the disclosure, the method comprises, moving one movable temporary attachment point, such as at least two movable temporary attachment points, towards said container; and temporarily attaching at least one wall or side to the movable temporary attachment point, thereby creating the determinable optical path length through the container.

In some examples of the disclosure, the method comprises modifying the shape of the container by pushing at least one side or wall a distance towards at least one second side or wall at one location thereby inflating the container at a second location creating the determinable optical path length through the container at the second location.

In some examples of the disclosure, the method comprises moving the light source head and/or detector head towards at least one wall or side of the container, and detecting when the light source head and/or detector head is in contact with the walls or sides of the container. The distance between the light source head and the detector head is creating the determinable optical path length through the container.

Alternatively, the distance between the light source head and the detector head at one side and a reflector at the opposite side of the container is creating the determinable optical path length through the container.

In some examples of the disclosure, modifying the shape of the container comprises positioning the container in an enclosure having walls and thereafter at least partly evacuating an atmosphere of the enclosure. The evacuation is expanding the container so that the walls or sides of the container make contact with the walls of the enclosure and thereby creating the determinable optical path length through the container.

In some examples of the disclosure, the method comprises positioning the light source head and the detector head at opposite sides of said determinable optical path length. The method may alternatively comprise, positioning the light source head and the detector head at the same side of the determinable optical path length and a reflective means at an opposite side.

In some examples of the disclosure, the method comprises utilizing a calibration routine based on using two laser beams, instead of determining said determinable optical path length.

Alternatively, the method may comprise a calibration routine based on measurements on a second container having a known gas concentration and a determinable optical path length equal to the determinable optical path length of the container with an unknown gas concentration.

In some examples of the method, the container is a tray with a flexible protection layer, such as a film, that is at least partly transparent. The method comprises pushing down the flexible protection layer by a mechanical means and a light signal is transmitted at an angle by the light source through the flexible protection layer of the tray and through a headspace and at a sidewall of the tray, detecting signal a reflected by the sidewall or transmitted through the sidewall.

In a further aspect, a system for measuring a concentration of a gas in a container having at least one flexible or variable side or wall is disclosed. The system comprises a light source head and a detector head. The system may further comprise means for making contact between an exterior of the walls or sides of the container, thereby creating a determinable optical path length through the container when contact is made. The system may also comprise a control unit for determining the concentration of a gas in a container based on detected light and the determined optical path length upon the contact.

In some examples of the disclosure, the means is at least one movable temporary attachment point to be attached to the exterior of the walls or sides of the container for pulling at least one side or wall of the container a distance relative at least one second side or wall to create the determinable optical path length through the container.

In some examples of the disclosure, the means are mechanical fixtures for pushing at least one side or wall of the container a distance towards at least one second side or wall at one location. The pushing at a first location may inflate the container at a second location, thus creating the determinable optical path length through the container at the second location upon the pushing.

In some examples of the disclosure, the means are movable to position the light source head and/or detector head in contact with at least one wall or side of the container. Further, the means comprises a sensor for detecting when the light source head and/or detector head is in contact with at least one wall or side of the container, thereby creating the determinable optical path length through the container.

In some examples of the disclosure, the means is an enclosure configured for the container to be positioned in. The means comprises a unit for at least partly evacuating an atmosphere of the enclosure wherein the container is expanded so that the walls or sides of the container can make contact with the walls of the enclosure. The at least partly evacuation of the atmosphere may create the determinable optical path length through the container.

In some examples of the disclosure, the light source head and the detector head are arranged at opposite sides of the determinable optical path length. Alternatively, the light source head and the detector head are arranged at the same side of the determinable optical path length and a reflective means at an opposite side of the container.

In some examples of the disclosure, the container is a tray with a flexible protection layer, such as a film, that is at least partly transparent. The means for making contact is a mechanical means for pushing down the flexible protection layer and the light signal is transmitted at an angle by the light source through the flexible protection layer of the tray and through a headspace and at a sidewall of the tray, the signal is reflected by or transmitted through the sidewall of the tray and is detected by the detector.

In some alternative examples in accordance with the disclosure, a method of determining a concentration of at least a first gas in a container having at least one flexible or variable side or wall is disclosed. The method comprises estimating an optical path length through the container. The method further comprise transmitting a first light signal between a light source and detector through the estimated optical path length and determining the concentration of the first gas in the container based on detected light of the first light signal and the optical path length.

In some further alternative examples in accordance with the disclosure, a system of determining a concentration of at least a first gas in a container having at least one flexible or variable side or wall is disclosed. The system comprises a light source and a detector for transmitting a first light signal through the container. The device further comprises a estimation unit for estimating an unknown optical path length that the first light signal travels through the container, and a control unit for determining the concentration of the at least first gas in the container based on detected light of the first light signal and the optical path length estimated by the estimation unit.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

The following disclosure focuses on examples of the present disclosure applicable to determining an optical path length in containers with flexible or variable and optically transparent or translucent walls. For example, this is advantageous for determining a concentration a gas by absorption spectroscopy of gaseous content in a container. However, it will be appreciated that the description is not limited to this application but may be applied to many other systems an optical path length need to be determined.

Absorption spectroscopy may either be a full absorption spectrum or a signal from at least one discrete wavelength.

It is assumed that the container that is subject to measurement comprises of a transparent, semi-transparent or translucent material. Alternatively, the container may have a window made of a transparent, semi-transparent or translucent material, which at least partially covers a wall or side of the container. The container may in some examples have two windows at opposite walls or sides.

The walls or sides of the container may either be non-rigid (flexible or soft) or the walls may be rigid but the process is such that the optical path length inside the containers vary in an unpredictable manner between individual containers or measurement situations. By determining the optical path length the light travels through the container the absorption of a gaseous content may be calculating using, for example, Beer-Lambert law. Alternatively and/or additionally, in some examples, instead of determining the optical path length after it has been fixed, a calibration or reference may be used to obtain the concentration of a gaseous content.

Figure 1:
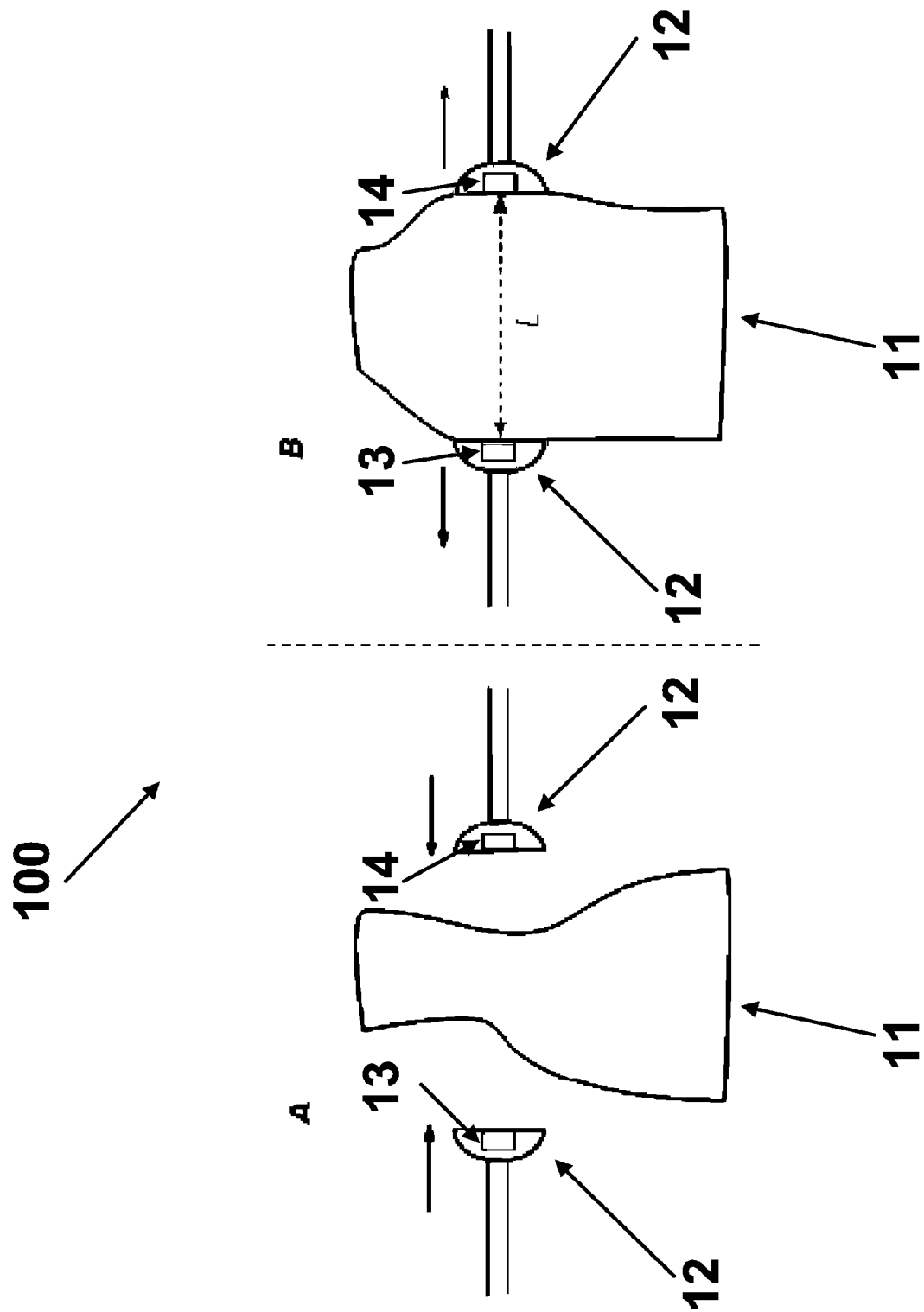
FIG. 1 is illustrating an example of creating a determinable optical path length through a container by pulling the walls or sides.

In an example illustrated in FIG. 1, a system 100 comprising of at least one movable temporary attachment points 12 that is attach to the container 11 during the measurement and a second fixed temporary attachment point.

Alternatively, the system 100 may comprise at least two movable temporary attachment points 12 at opposite sides of a determinable optical path length to be created.

Attachment may be accomplished by, but is not limited to, suction (vacuum), adhesives, or electrostatics. An optical measurement apparatus comprising of at least one light source head 13 and at least one detector head 14 mounted in, on or beside the temporary attachment points 12. The light source head 13 and the detector head 14 are mounted in a manner that when the distance between some given points for the temporary attachment points 12 is known, then the distance L between the light source head 13 and detector head 14 is also known. Further, when the movable temporary attachment points 12 are attached to the container 11, the light source head 13 and detector head 14 will be in contact with, or in very close vicinity to, the container walls, or with known distance to the walls. Prior to performing the measurement, the container 11 is placed between the temporary attachment points 12, and at least one of attachment points 12 is then moved toward the container 11 until a sufficient number of them make contact with the container 11. When the temporary attachment points 12 have attached to the container walls, the temporary attachment points 12 may mechanically be withdrawn, bringing the container walls apart, to a pre-determined optical path length having a distance L. When separating the walls or sides of the container 11 the shape of the container 11 is modified, hence creating an determinable optical path length having a distance L.

Alternatively, the determinable optical path length may be taken as the distance when the temporary attachment points 12 first make contact with the container with no further adjustments by separating the walls or sides by pushing them apart.

FIG. 1A is depicting a situation before measurement where the at least one temporary attachment points 12 are about to attach to the container. FIG. 1B is illustrating a situation during measurement wherein the temporary attachment points 12 are attached to container 11.

In another example, the light source head and detector head are mechanically mounted so that at least one of them can be moved in at least one degree of freedom, allowing the light source head and the detector head to come in close contact with the container walls. Moreover, the distance between the light source head and the detector head may be known, by means of but not limited to, mechanical calibration of the distance at all possible positions, or by some means of electronic or optical determination of their respective positions and successive calculation of the distance between them. Prior to performing the measurement, the container is placed between the light source head and the detector head, and the light source head and/or detector head are then moved toward the container until both of them make contact with the container. In an automated process, such as an autosensing process, there is some means to detect when the light source head and the detector head make contact with the container wall, e.g., by means of but not limited to, micro switches, electrical, or optical methods.

Alternatively, in some examples the light source head and detector head is mounted at a fixed distance. Prior to measuring the container is forced in-between the light source head and detector head. The fixed distance between the light source head and the detector head is such that the contained occupies substantially all of the space and the laser and detector head come in close contact with the container walls. Thus the path length inside the container is known.

Figure 5:
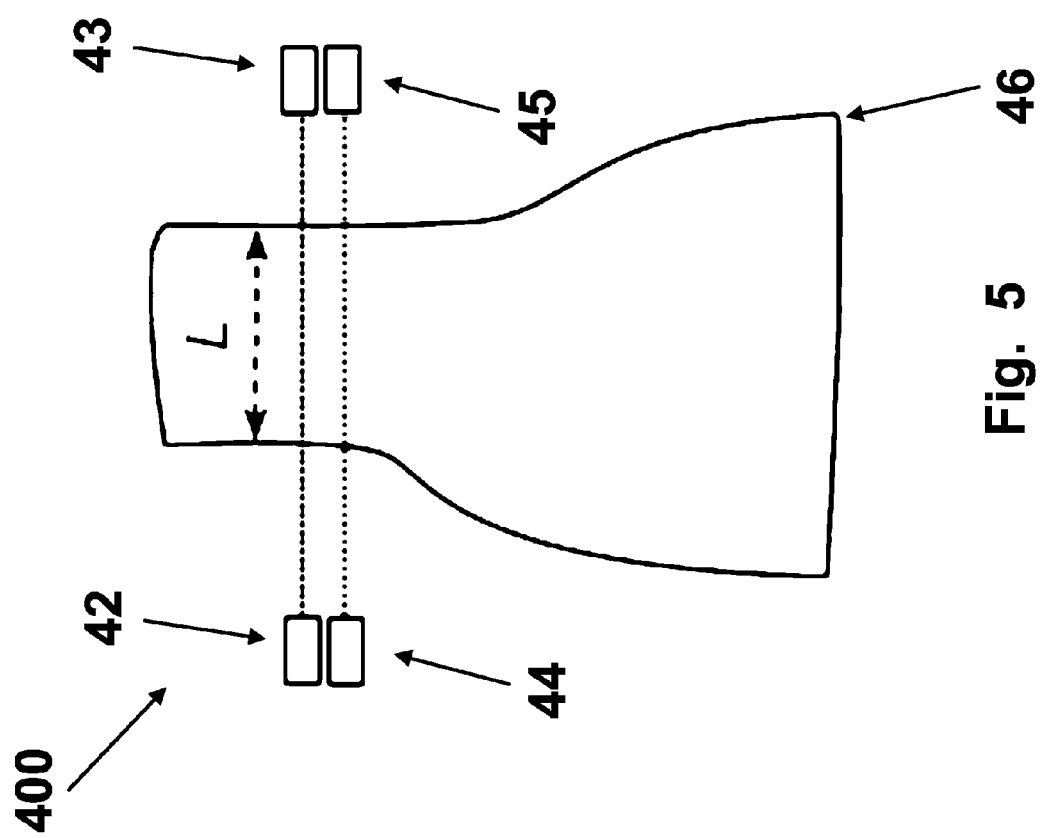
FIG. 5 is illustrating an example of a system including a parallel channel for measuring a second gas.

Additionally, in some examples, instead of determining the optical path length through the container after the optical path length has been fixed by temporary attachment points, a calibration method as described in relation to FIG. 5 may be used to establish the concentration of a gaseous content in the container 11.

Additionally and/or alternatively, in some examples of the system 100 depicted in FIG. 1, instead of directly determining the optical path length L inside the container 11, it is possible to obtain the gas concentration by means of calibration. The calibration may be performed by performing measurements on one or more containers with a known concentration of the gas. The recorded signals obtained by the detector correspond to particular gas concentrations in the container. The gas concentration may then be subsequently determined on containers 11 with an unknown gas concentration without directly establishing the optical path length, as long as the measurement conditions are traceable to the measurement conditions used during the calibration. One way of establishing traceable measurement conditions is to use technique disclosed in conjunction with FIG. 1.

Figure 2:
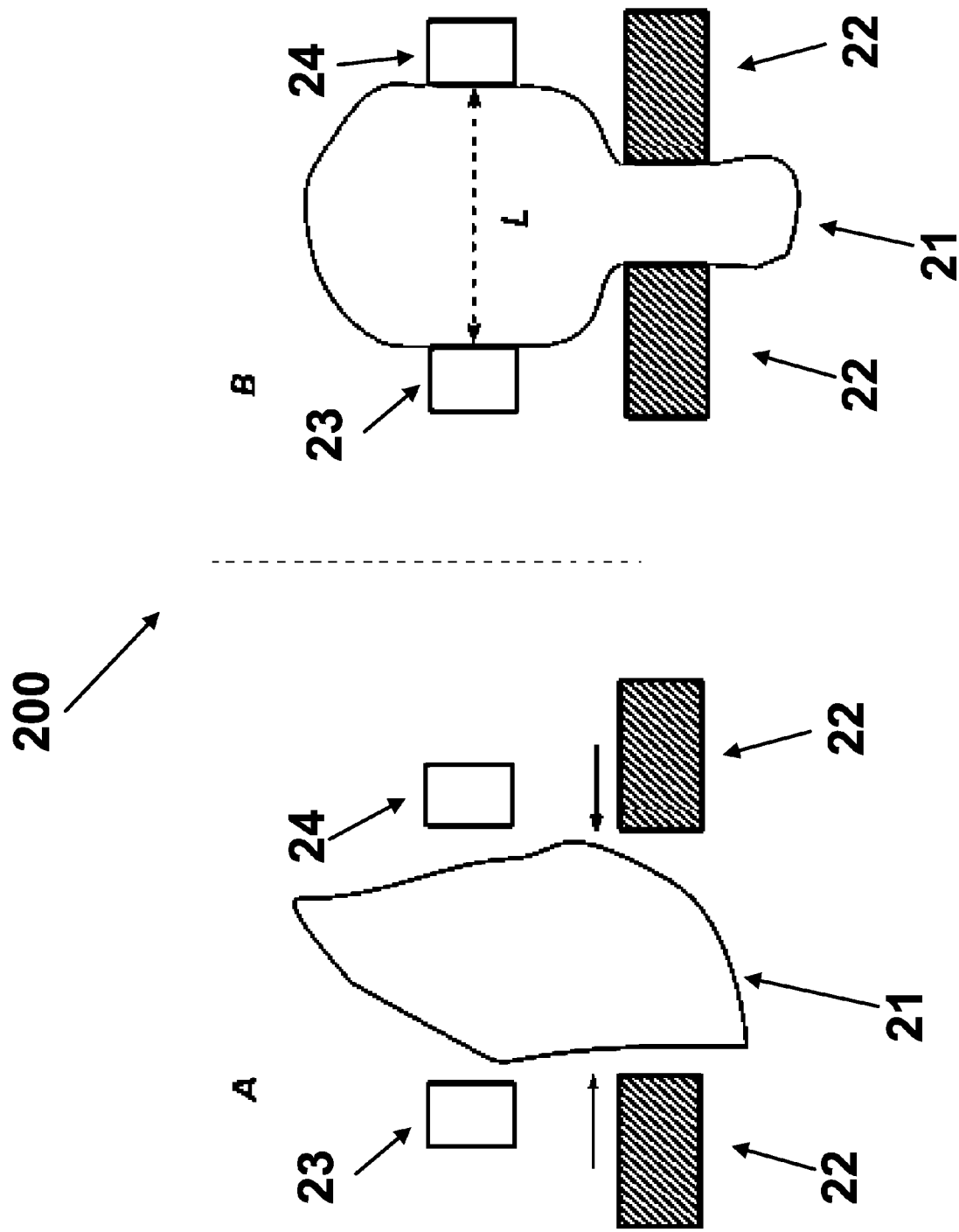
FIG. 2 is illustrating an example of creating a determinable optical path length through a container by pushing the walls or sides.

In another example illustrated in FIG. 2, a system 200 comprising a container 21 that is subject to measurement is placed in a mechanical fixture 22 which applies a mechanical pressure to the walls at one location of the container 21. The increased pressure will inflate another second location of the container and push the container walls of the second location of the container 21 against the light source head 23 and detector head 24. The distance L of the separated walls may be determined as the distance L between the light source head 23 and the detector head 24 since this distance may be known. Because the container volume after inflation occupies substantially all of the space between the light source head 23 and detector head 24, the optical path length inside the container 21 may be determined.

FIG. 2A is depicting a situation before measurement where a container 21 is placed between mechanical fixtures 22. FIG. 2B is depicting a situation during a measurement where container 21 is inflated by mechanical force.

The area of the mechanical fixture 22 which exerts a pressure on the container 21 may be a point, clamp-like or constructed like an iris.

The container may here be a flexible bag or a semi rigid tray. A semi rigid tray may, for example, be made of thin plastic which flex enough for the shape to be modified by exertion of an external pressure on at least one wall of the tray.

Additionally, in some examples, instead of determining the optical path length through the container after the optical path length has been fixed by temporary attachment points, a calibration method as described in relation to FIG. 5 may be used to establish the concentration of a gaseous content in the container 21.

Additionally and/or alternatively, in some examples of the system 200 depicted in FIG. 2, instead of directly determining the optical path length L inside the container 21, it is possible to obtain the gas concentration by means of calibration. The calibration may be performed by performing measurements on one or more containers with a known concentration of the gas. The recorded signals obtained by the detector correspond to particular gas concentrations in the container. The gas concentration may then be subsequently determined on containers 21 with an unknown gas concentration without directly establishing the optical path length, as long as the measurement conditions are traceable to the measurement conditions used during the calibration. One way of establishing traceable measurement conditions is to use technique disclosed in conjunction with FIG. 2.

Figure 3:
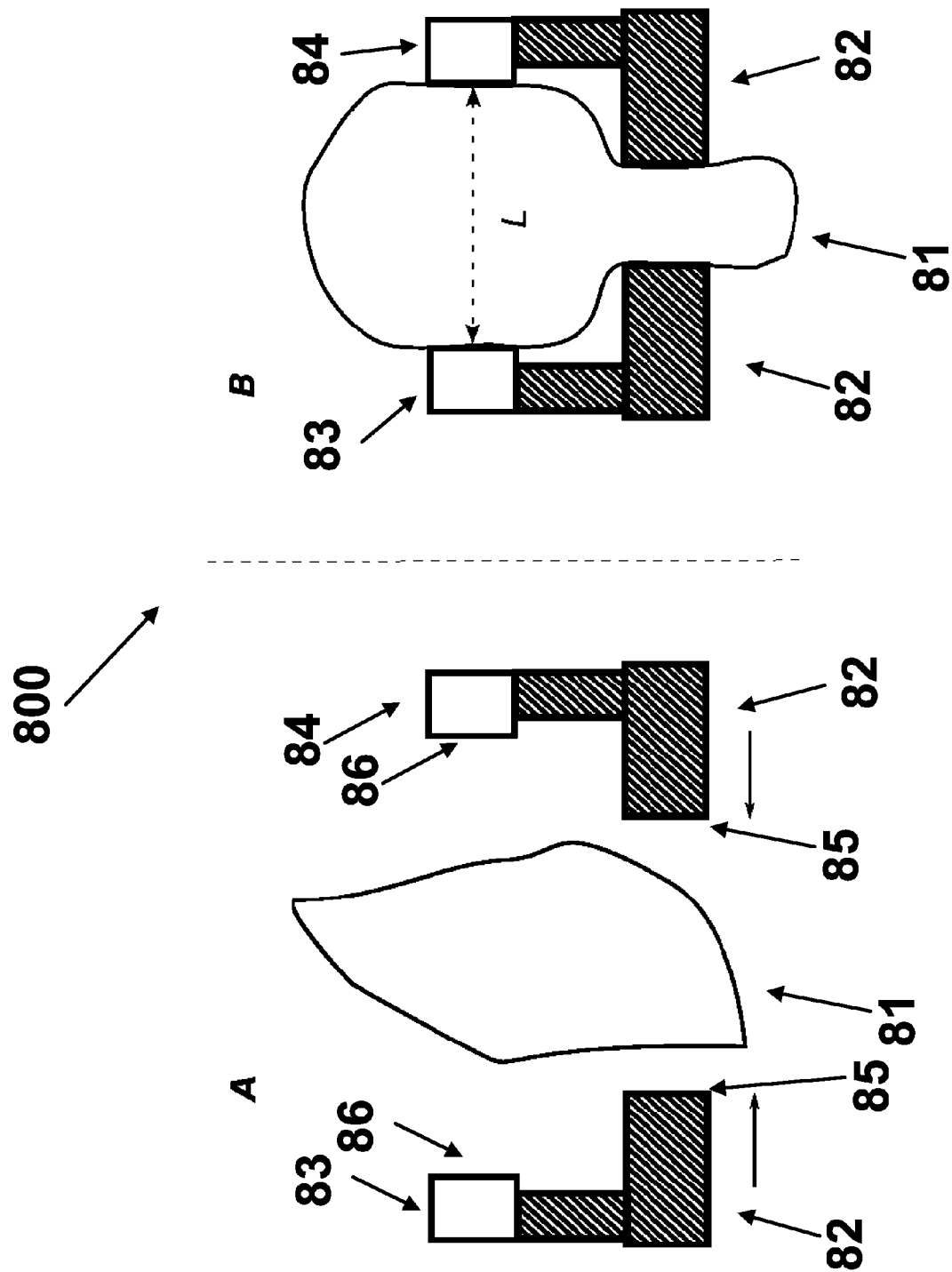
FIG. 3 is illustrating another example of creating a determinable optical path length through a container by pushing the walls or sides.

FIG. 3 illustrates a system 800 comprising a mechanical fixture 82 similar to the mechanical fixture 22 in FIG. 2. The light source head 83 and the detector head 84 are attached to the mechanical fixture 82. The light source head 83 and the detector head 84 have areas 86 configured to be positioned against the walls of the container 81. These areas 86 may either be aligned with the areas 85 of the mechanical fixture 83 which are configured to exert an external pressure on the container 81. Alternatively, the areas 86 of the detector head 84 and light source head 83 may be positioned a distance from the areas 85 of the mechanical fixture 83, as illustrated in FIG. 3. In this way the areas 86 may come into contact with the walls of the container 81 when the increased pressure on a first location of the container 81 inflates a second location of the container. When the areas 86 are in contact with the walls of the container 81, the optical path length L may be determined. FIG. 3A is illustrating before measurement and FIG. 3B is illustrating when the second location has been inflated by the exert of an external pressure form the mechanical fixtures 82.

Additionally, in some examples, instead of determining the optical path length through the container after the optical path length has been fixed by temporary attachment points, a calibration method as described in relation to FIG. 5 may be used to establish the concentration of a gaseous content in the container 81.

Additionally, in some examples, instead of determining the optical path length through the container after the optical path length has been fixed by temporary attachment points, a calibration method as described in relation to FIG. 5 may be used to establish the concentration of a gaseous content in the container 81.

Additionally and/or alternatively, in some examples of the system 800 depicted in FIG. 3, instead of directly determining the optical path length L inside the container 81, it is possible to obtain the gas concentration by means of calibration. The calibration may be performed by performing measurements on one or more containers with a known concentration of the gas. The recorded signals obtained by the detector correspond to particular gas concentrations in the container. The gas concentration may then be subsequently determined on containers 81 with an unknown gas concentration without directly establishing the optical path length, as long as the measurement conditions are traceable to the measurement conditions used during the calibration. One way of establishing traceable measurement conditions is to use technique disclosed in conjunction with FIG. 3.

Figure 4:
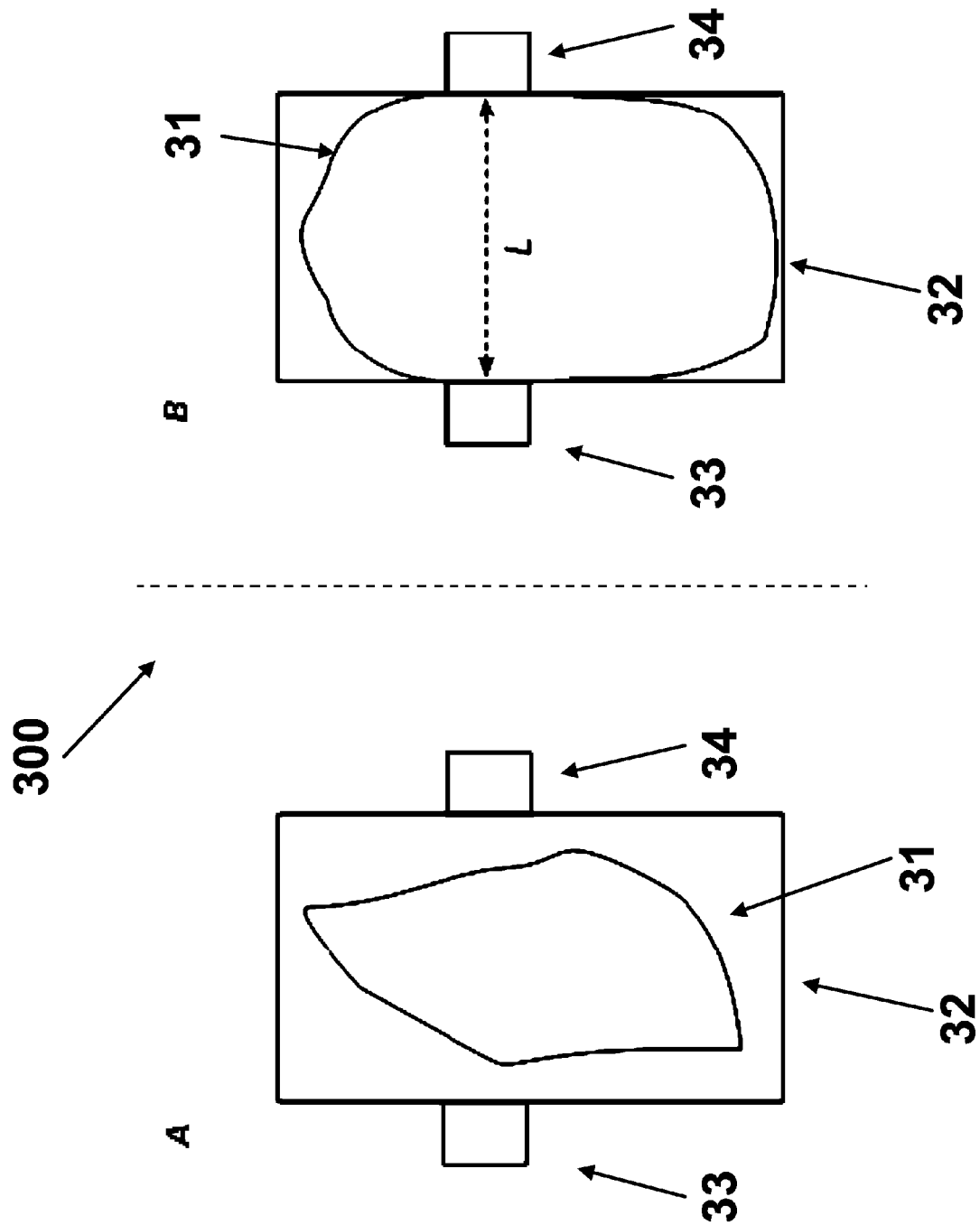
FIG. 4 is illustrating an example of creating a determinable optical path length through a container by positioning it in an evacuable enclosure.

In FIG. 4, a system 300 comprising a container 31 that is subject to measurement is illustrated. The container 31 is placed inside an enclosure 32 surrounded by walls in a plurality, but not necessarily all, spatial directions. The light source head 33 and the detector head 34 are placed at least one of the walls of the enclosure 32. Prior to performing the measurement, the atmosphere in the enclosure 32 is at least partly evacuated, creating an at least partial vacuum inside the enclosure. The lower atmospheric pressure in the enclosure causes the volume in the container to expand and the container walls to make contact with the enclosure walls, and thus make contact with the light source head 33 and detector head 34. Since the distance L between the enclosure walls may be known, the optical path length inside the container 31 may also be known in this configuration.

FIG. 4A is depicting a situation before measurements when the container 31 has been placed in enclosure 32. FIG. 4B is depicting a situation after the atmosphere in the enclosure 32 has been at least partly evacuated.

Additionally, in some examples, instead of determining the optical path length through the container after the optical path length has been fixed by temporary attachment points, a calibration method as described in relation to FIG. 5 may be used to establish the concentration of a gaseous content in the container 31.

Additionally and/or alternatively, in some examples of the system 300 depicted in FIG. 4, instead of directly determining the optical path length L inside the container 31, it is possible to obtain the gas concentration by means of calibration. The calibration may be performed by performing measurements on one or more containers with a known concentration of the gas. The recorded signals obtained by the detector correspond to particular gas concentrations in the container. The gas concentration may then be subsequently determined on containers 31 with an unknown gas concentration without directly establishing the optical path length, as long as the measurement conditions are traceable to the measurement conditions used during the calibration. One way of establishing traceable measurement conditions is to use technique disclosed in conjunction with FIG. 4.

Alternatively, in the examples illustrated and disclosed in relation to FIGS. 1 to 4, the light source head and the detector head may be placed at the same location and a reflective surface at the opposite side of the container. In such a configuration the light will be reflected back by the reflective surface and the light will travel a distance of twice the optical path length. Hence the accuracy of the measured concentration may increase.

In another example, the light source head and detector head are mounted in a fixed configuration and the container, such as a bag or a tray, subject to measurement is placed in between or in front of to the light source head and detector head and a gas-probing light beam is sent through the container. Alternatively the gas probing beam is sent through the container and is reflected back. Alternatively of having the light beam travelling through the container is to reflect the light beam against a, for the light, reflective surface inside the container. The reflective surface may be an inner surface of the container itself.

The unknown distance the light beam travels through the container may be measured with the help of wall localization using an imaging system utilizing, e.g., by means of but not limited to, focus detection, spot detection of probing laser beam or reference beam, or image analysis. The focusing detection system, rangefinder, may use, but not limited to, electroacoustic or electronic means. The imaging system can be positioned on, but not limited to, the same side as the light source head or above the container.

In another example, the light source head and detector head are mounted in a fixed configuration and the container subject to measurement is placed inbetween or in front of to the the light source head and detector head and the gas-probing light beam is sent through the container, alternatively through and reflected back. The distance the light is travelled through the container is estimated utilizing ranging technologies for determining the positions of the walls of the containers or a reflector inside the container. Ranging methods include, e.g. but not limited to laser rangefinder with pulsed laser or triangulation, or ultra sound eco ranging.

FIG. 5 illustrates an example of a dual channel system 400. A gas-probing light is sent by a first light source head 42 through a container 46 having unknown dimensions, such as an unknown optical path length. The light is detected by a first detector head 43 which may be positioned opposite the first light source head 42. Alternatively, the first light source head 42 and the first detector head 43 may be located at the same side and a reflector is positioned at the opposite side.

A parallel gas-measurement channel sending light from a second lights source head 44 to a second detector head 45 is utilized to measure the gas-probing light distance by means of absorption spectroscopy of a second gas present in the container. This second gas has a known concentration, e.g. but not limited to water vapour or carbon dioxide. The second channel laser beam overlaps or at least travels a similar path as the primary gas-sensing laser light through the container 46. Alternatively, the second light source head 44 and the second detector head 45 may be located at the same side with a reflector positioned at the opposite side.

An advantage with this method is that by calibrating against the second channel, there is no need to determining the optical path length L through the container 46.

Figure 6:
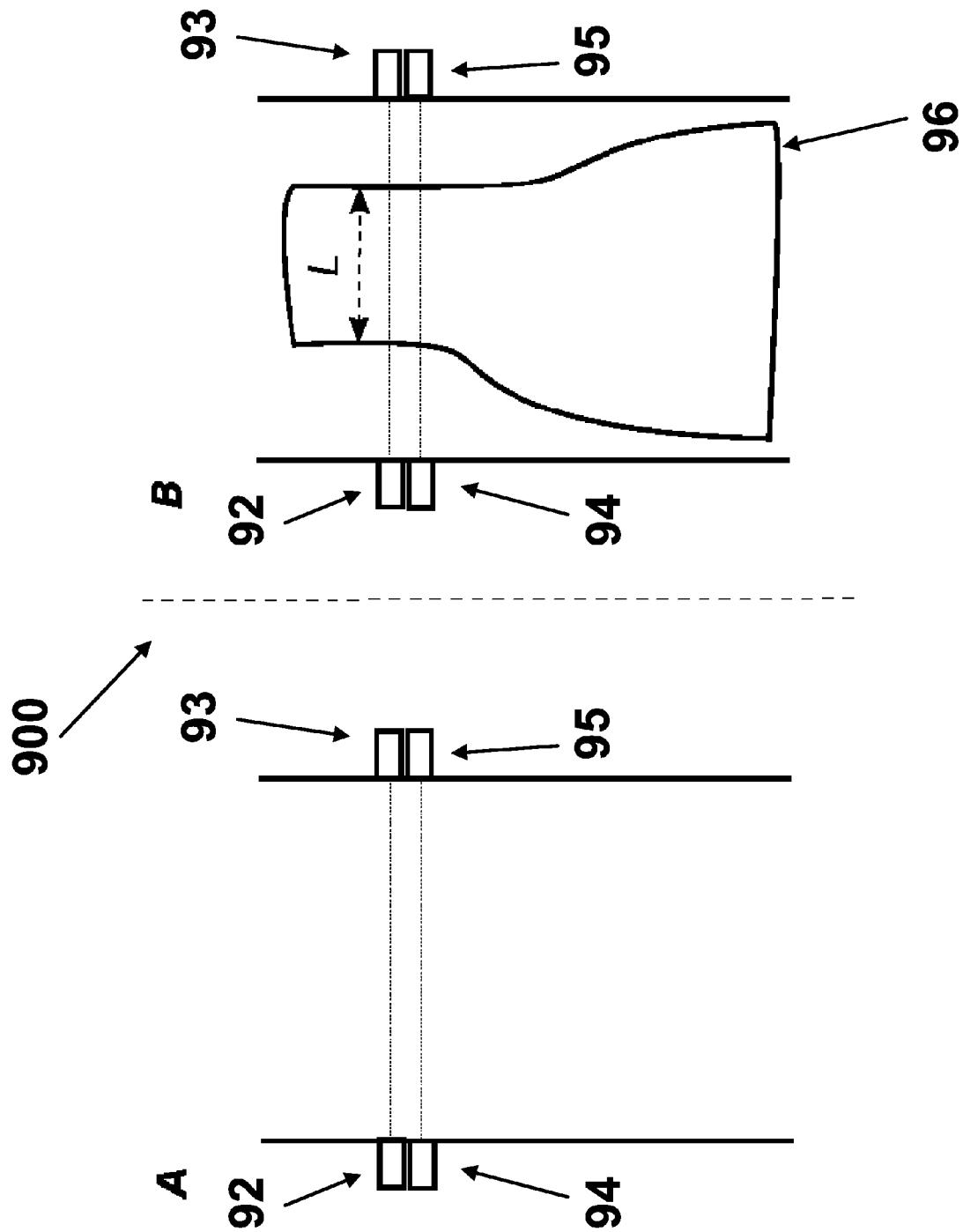
FIG. 6 is illustrating another example of a system including a parallel channel for measuring a second gas.

FIG. 6 illustrates another example of a system 900 having dual channels. A first light source head 92 and a second light source head 94 is mounted opposite a first detector head 93 and a second detector head 95. The light source heads and the detector heads are mounted in a fixed configuration with a known distance sending a beam through, for example, an enclosure or between to walls. Alternatively, in some examples, the light source heads and the detector heads may be mounted at the same side and a reflector may be mounted at the opposite side.

FIG. 6A illustrates a system 900 subject to a measurement of a primary gas which concentration is to be estimated. FIG. 6B illustrates system 900 with a container 96 positioned in the path of the beams. In this example, the second light source head 94 and the second detector head 95 forms a second parallel gas-sensing channel. This second channel is configured to use laser absorption spectroscopy to measure at least one additional gas other than the primary gas. This at least one additional gas may either not be present or at least present with a known concentration inside the sealed container. The at least one additional gas should be present naturally or by choice in the surrounding of the container. The difference in gas absorption of the second channel in the system 900 with the container 96 present or not present allows a measure of the distance the light pass through the gas inside the container. In this configuration, the second channel laser beam overlaps or at least travels a similar path as the primary gas-sensing laser light.

Figure 7:
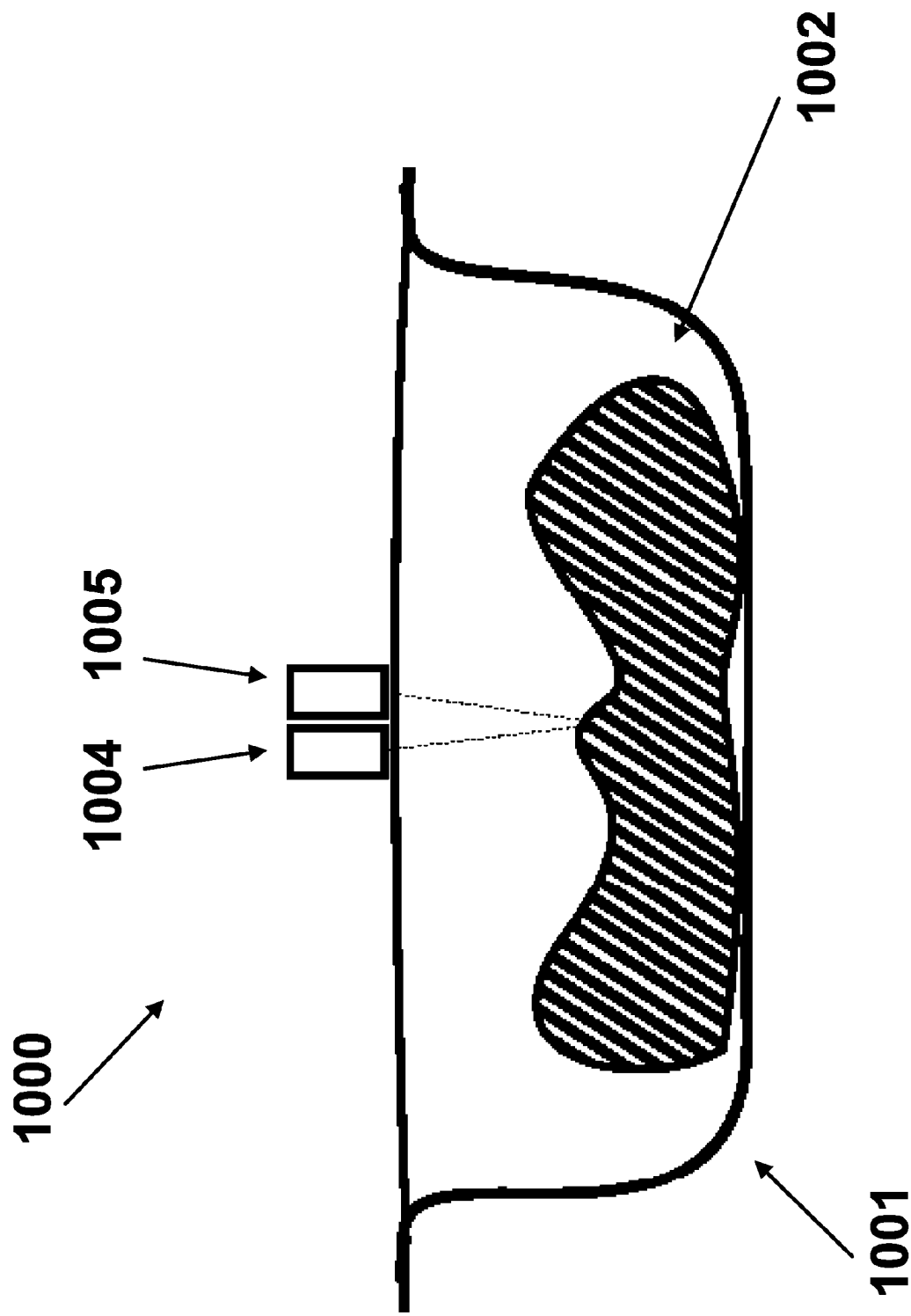
FIG. 7 is illustrating reflectance measurements on a tray.

FIG. 7 illustrates an example of a system 1000 for measuring the concentration of at least one gas inside a tray 1001, where the optical path length is unknown. A first light source and a first detector are positioned at a location 1004 outside of the tray 1001 and a second light source and a second detector is positioned at a location 1005 outside of the tray 1001. The first light source and the first detector are configured for measuring a primary gas which concentration is to be estimated. The second light source and the second detector are configured for measuring at least one second gas with known concentration.

The at least one second gas, e.g. but not limited to water vapour or carbon dioxide, has a known concentration.

The light from the first and second light source is transmitted through a wall of the tray 1001. The light may either be reflected back by the content 1002 in the container or by a separate reflective surface positioned at the surface of the content 1002.

Additionally and/or alternatively, in some examples the light from the first and second light source is transmitted through the wall 1001 and reflected back by a wall of the tray.

In some examples, the reflective area may be an inner surface of a side wall of the tray. To illuminate an inner surface of the side wall and to detect back reflected light, the light beams are directed through the top film of the tray and through the headspace, at a sidewall of the tray at an angle. The detector or detectors is arranged at an angle to collect the light reflected back. This configuration ensures that the contents of the package may not interfere with the light beam.

Alternatively, in some examples, depending on whether the sidewall of the tray is transparent or not, the detector or detectors may be used in transmission mode. In transmission mode the detector or detectors are positioned outside of the sidewall and arranged so as to detect the light that has been transmitted at an angle through a top surface of the tray, through the headspace and through a sidewall.

The light of the first beam and the light of the second beam may be transmitted into the tray as parallel beams, overlap in the same beam path or at least travels a similar path. If the beams overlap in the same beam path, only one detector may be needed. If the same detector is used, the beams may be separated by modulation of the frequencies or by using filters in front of the detector.

Since the concentration of the at least second gas is known, the optical path length in the tray 1001 may be determined or calibrated for. Hence the concentration of the primary gas can be estimated.

For obtaining parallel or overlapping beam paths the configuration of the positions of the light sources and the detectors may be varied and combined with further components such as partially transparent mirrors and filters.

Figure 8:
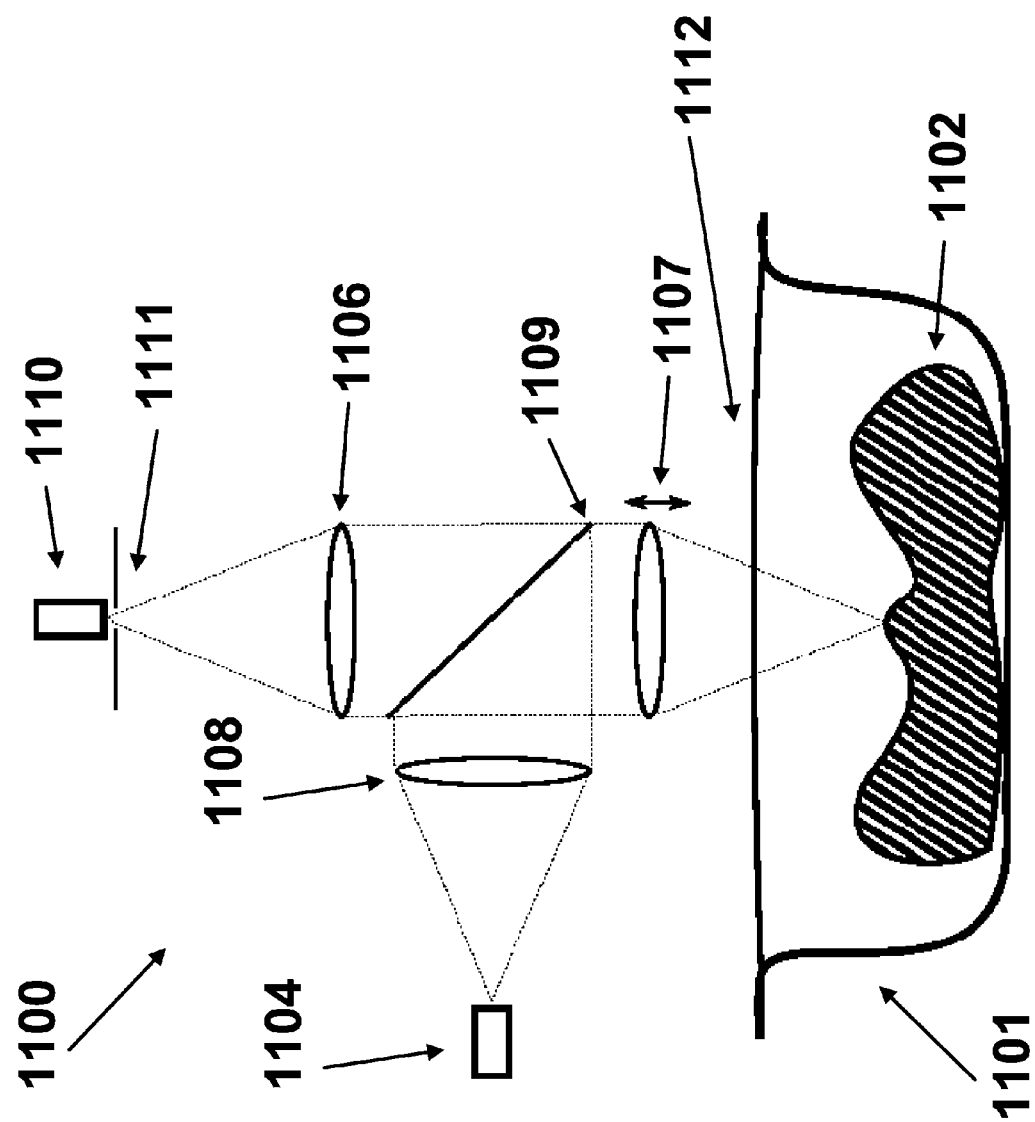
FIG. 8 is illustrating measurements on a tray using an exemplary confocal configuration.

FIG. 8 illustrates a system 1100. A laser head 1104 and a detector head 1110 are placed in a confocal configuration using a partially transparent mirror 1109 and a lens assembly 1106 and 1107. At the detector 1110, there is a pinhole 1111 which suppresses light reflecting from points other than the confocal point. The objective lens 1107 is movable along the direction of the optical axis. To find the optical path length inside the container, an automated system moves the objective lens 1107 until a maximum signal is detected by the detector 1110, which corresponds to when the objective lens 1107 is focused on the far surface of a content 1102 or added reflective area inside the container 1101. Since the working distance of the focal length of the objective lens 1107 is known, and the distance of the objective lens 1107 from the first surface 1112 of the container 1101 can be known, the optical path length inside the container 1101 can be determined.

In some examples, the reflective area may be an inner surface of a side wall of the tray. To illuminate an inner surface of the side wall and to detect back reflected light, the whole confocal arrangement is arranged at an angle to emit light towards the inner surface of the sidewall and to detect light reflected back from the inner surface of the sidewall. This configuration ensures that the contents of the package will not interfere with the light beam.

Figure 9:
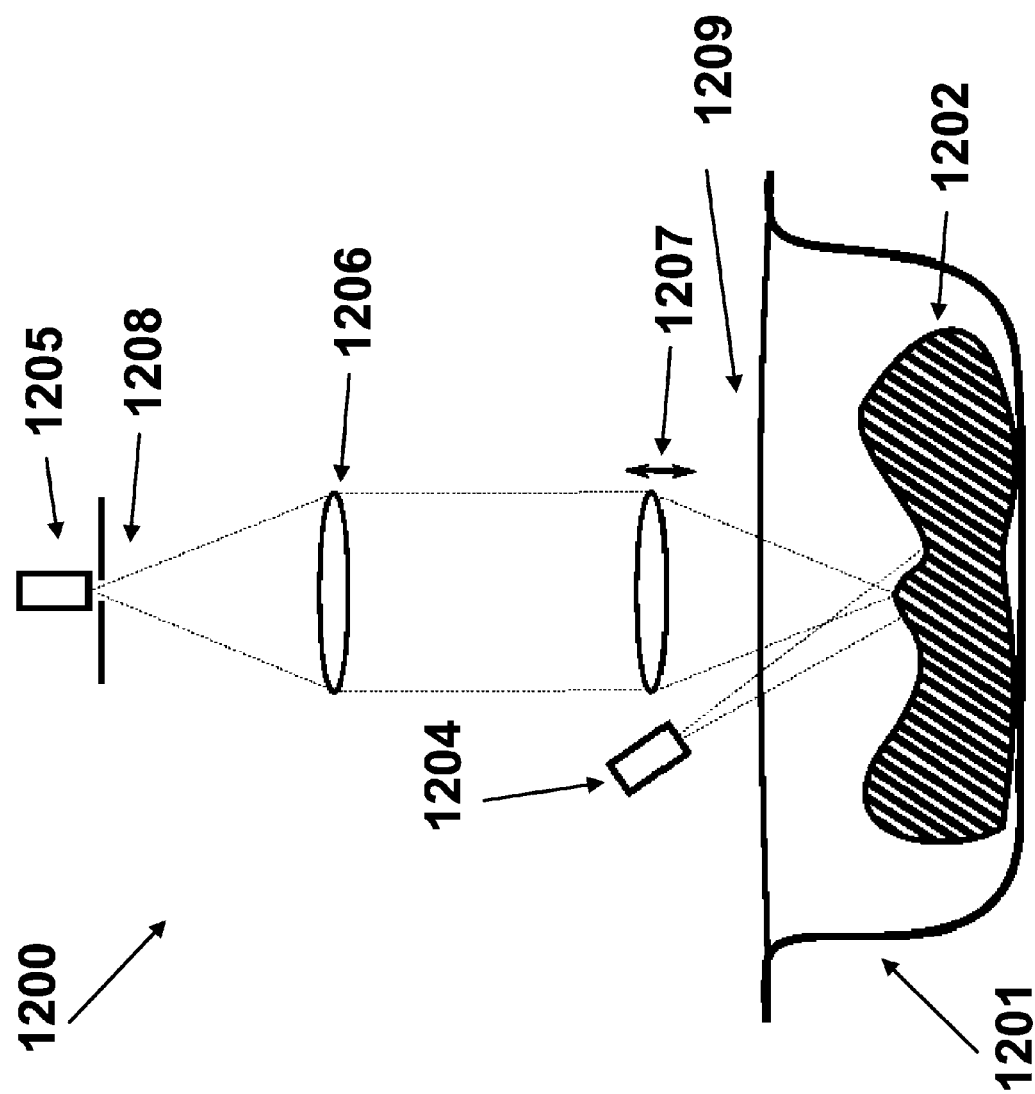
FIG. 9 is illustrating measurements on a tray using another exemplary confocal configuration.

Alternatively, in an example illustrated in FIG. 9, a laser 1204 illuminates the back surface of a container 1201, or the content 1202 or an added reflective area inside the container 1201. The laser 1210 is separated from the confocal arrangement which includes a detector 1205, a pin hole 1208, a leans 1206 and a movable objective lens 1207. The illumination is done from a well-defined position in relation to the confocal arrangement and a first wall 1209 of the container 1201. In some examples, the reflective area may be an inner surface of a side wall of the tray. To illuminate an inner surface of the side wall and to detect back reflected light, the light beam is directed through the top film of the tray and through the headspace, at a sidewall of the tray at an angle. The confocal arrangement is also arranged at an angle to detect light reflected back from the inner surface of the sidewall. This configuration ensures that the contents of the package will not interfere with the light beam.

The disclosure further relates to a method of determining a concentration of at least a first gas in a container having at least one flexible or variable side or wall, the method comprises estimating an optical path length through the container. The method also includes transmitting a first light signal between a light source and a detector through the estimated optical path length and determining the concentration of the first gas in the container based on detected light of the first light signal and the optical path length.

In some examples, the method comprises positioning the light source and detector at a side of the container and a reflector arranged for reflecting the first light signal at an opposite side of the container.

In some examples, estimating the optical path length is based on transmitting a second light signal between a second light source and the detector for measuring absorption spectra of a second gas with a known concentration.

In some examples, estimating the optical path length is based on transmitting a second light signal between a second light source and a second detector for measuring an absorption signal of a second gas with a known concentration.

In some examples, the second gas is inside the container and/or outside the container.

In some examples, the second signal is transmitted the same optical path length as the first light signal In some examples, the estimation of the optical path length and the transmitting of a first light signal is performed using a confocal configuration.

In some examples, estimating the optical path length through the container is based on utilizing a range finder with pulsed laser or triangulation, or ultra sound echo ranging.

In some examples, estimating the optical path length through the container is based on utilizing a wall localization imaging method, wherein the wall localization imaging method is based on focus detection, or spot detection or image analysis.

The disclosure also relates to a system of determining a concentration of at least a first gas in a container having at least one flexible or variable side or wall. The system comprises a light source for transmitting a first light signal through the container and a detector for detecting transmitted light. The system further includes an estimation unit for estimating an unknown optical path length that the first light signal travels through the container and a control unit for determining the concentration of the at least first gas in the container based on detected light of the first light signal and the optical path length estimated by the estimation unit.

In some examples the estimation unit comprising a second light source for transmitting a second light signal through a second gas with a known concentration over a known optical path length.

In some examples the control unit is further configured to estimate the unknown optical path length based on an absorption signal obtained by the second light signal.

In some examples the system comprises a movable objective lens and that the objective lens, the detector and the light source and the estimation unit has a confocal configuration.

In some examples the estimation unit is a range finder with pulsed laser or triangulation, or ultra sound eco ranging.

In some examples the estimation unit is a wall localization system, and wherein the wall localization imaging system is based on focus detection, or spot detection, or image analysis.

EXAMPLES

Three different examples of measurement solutions of oxygen sensing inside flexible packages were performed. These three experiments were carried out to demonstrated increased performance regarding both accuracy and variation.

TABLE 1

|  | New method | Input sample |
|---|---|---|
| Autosensing | 0.63 | 3.65 |
| Pulling | 0.64 | 4.05 |
| Push | 0.60 | 3.95 |
| True Value | 0.6 | 0.6 |

The studied sample was a bag of pasta. The oxygen content was measured with a reference technology to 0.6% O2, in good agreement with the laser technology results.

The laser is placed within the laser head, which makes it impossible to place the bag firmly against the laser. This yields an offset since the laser light has been passing through a 14 mm long column of air, with 20.9 percent oxygen, before passing through the bag. The absorption due to the distance between the laser and the end of the laser module is removed from the obtained absorption signal.

Example of Pulling

The configuration was similar as to the configuration illustrated in FIG. 1. The laser head and detector were set a known distance apart (48.1 mm). To illustrate the improved performance of using a pulling technology, i.e. the sample walls in close contact to laser and detector, two sets of measurements were performed.

In the first set the bag was randomly placed between the laser head and detector and measured during one second without having the light source head and detector head in contact with the container. In the second set the bag was stretch out/pulled by external means to fill the void between the light source head and detector head and also measured in similar random position of the bag. 15 measurements with the bag randomly placed and then stretched were made.

Figure 10:
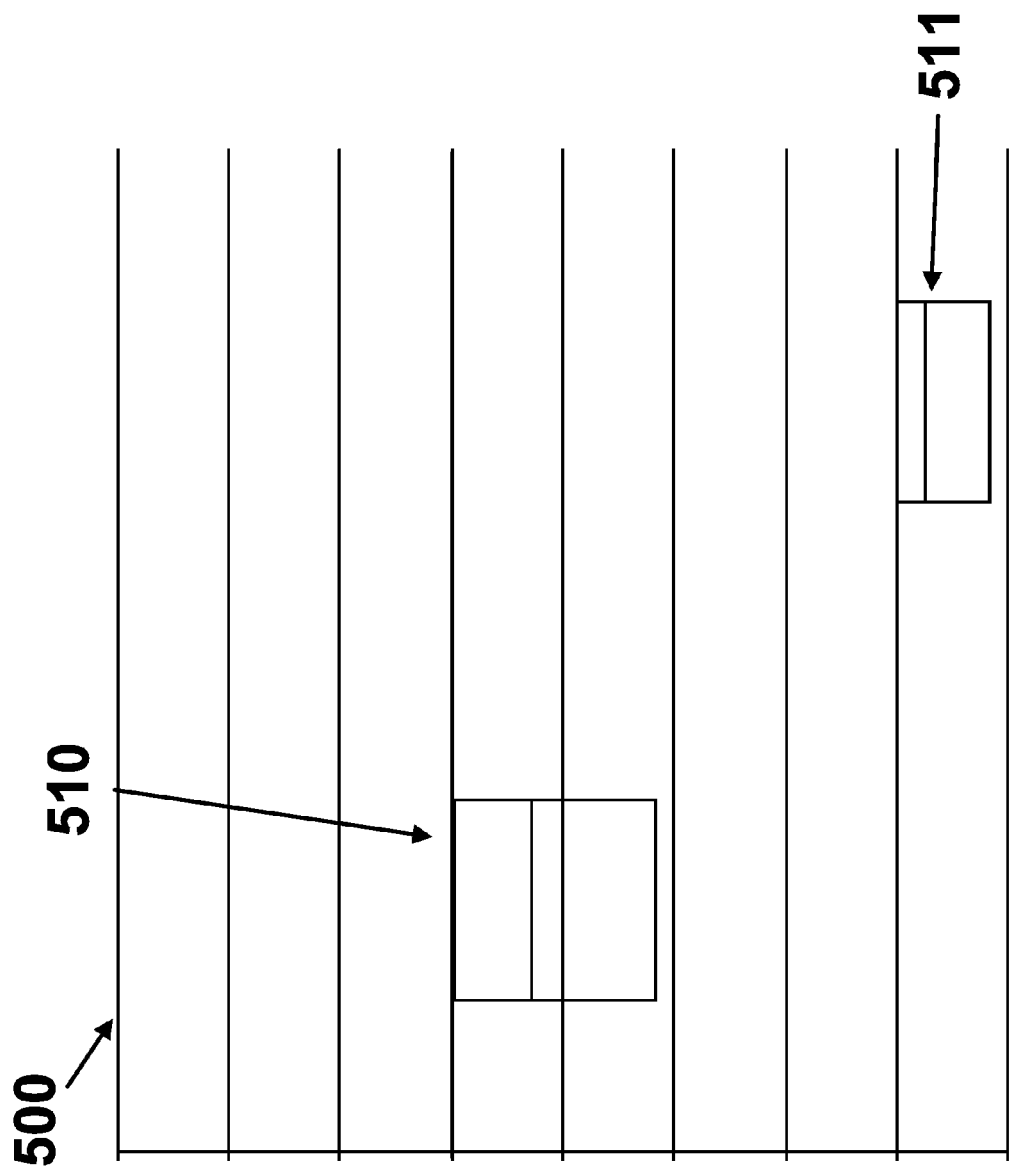
FIG. 10 is depicting results from an exemplary experiment of a pulling configuration.

The results of the two measurement sets are presented in FIG. 10 in a box plot 500. A clear improvement of the accuracy and the variation of the measured values are obtained by positioning the walls with external means, e.g. pulling 511 or using suction compared to not pulling 510.

FIG. 10 is demonstrating the improved performance of gas sensing as the sample walls are externally positioned close to the light source head and detector head. The sample oxygen content of the container was 0.6% O2.

Example of Pushing

The configuration was similar as to the configuration illustrated in FIG. 2. The light source head and detector head were set a known distance apart (64.3 mm). To illustrate the improved performance of using a pushing technology, i.e. the sample walls in close contact with the light source head and detector head, two sets of measurements were performed.

In the first set the bag was randomly placed between the laser head and detector and measured during one second.

In the second set the bag was pressed together at the bottom part so that the top part would fill the space between the laser head and detector. 15 measurements with the bag randomly placed and then pushed were made.

Figure 11:
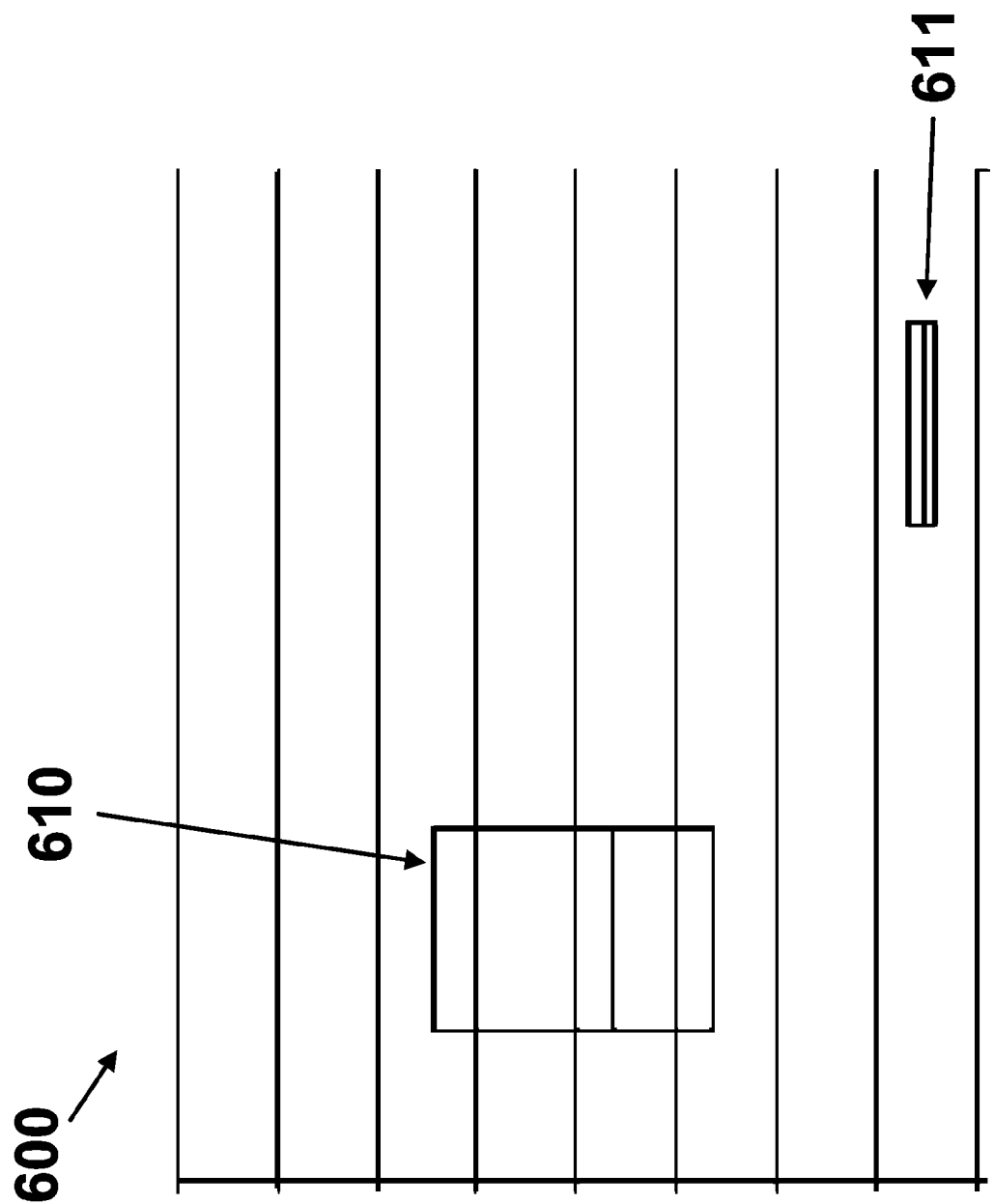
FIG. 11 is depicting results from an exemplary experiment of a pushing configuration.

The results of the two measurement sets are presented in FIG. 11 in a box plot 600. A clear improvement of the accuracy and the variation of the measured values are obtained by pushing 611 the walls to a close proximity to the light source head and detector head compared to not pushing 610.

FIG. 11 is demonstrating the improved performance of gas sensing 611 as the sample walls are pushed towards the light source head and detector head by pressing on the sample at another location. The sample oxygen content of the container was 0.6% O2.

Example of Auto Sensing

Measurements were performed to illustrate the improved performance by moving the laser and detector in close distance of the package walls and by detect the distance compared to having the laser and detector fixed.

The laser head and detector were set 64.7 mm apart. The detector was then moved in direction in order to close the distance to the laser head and then back to its original position. The distance between the laser head and detector was re-measured. This procedure was repeated five times and resulted in mean distance of 64.7 mm. For every measurement the bag was randomly placed between the laser head and detector, in such way that the bag was in contact with the laser head and measured during one second. For the same random position the detector was moved in direction towards the laser head until it was in contact with the bag. The value was re-measured and the distance between the laser head and detector was measured.

Figure 12:
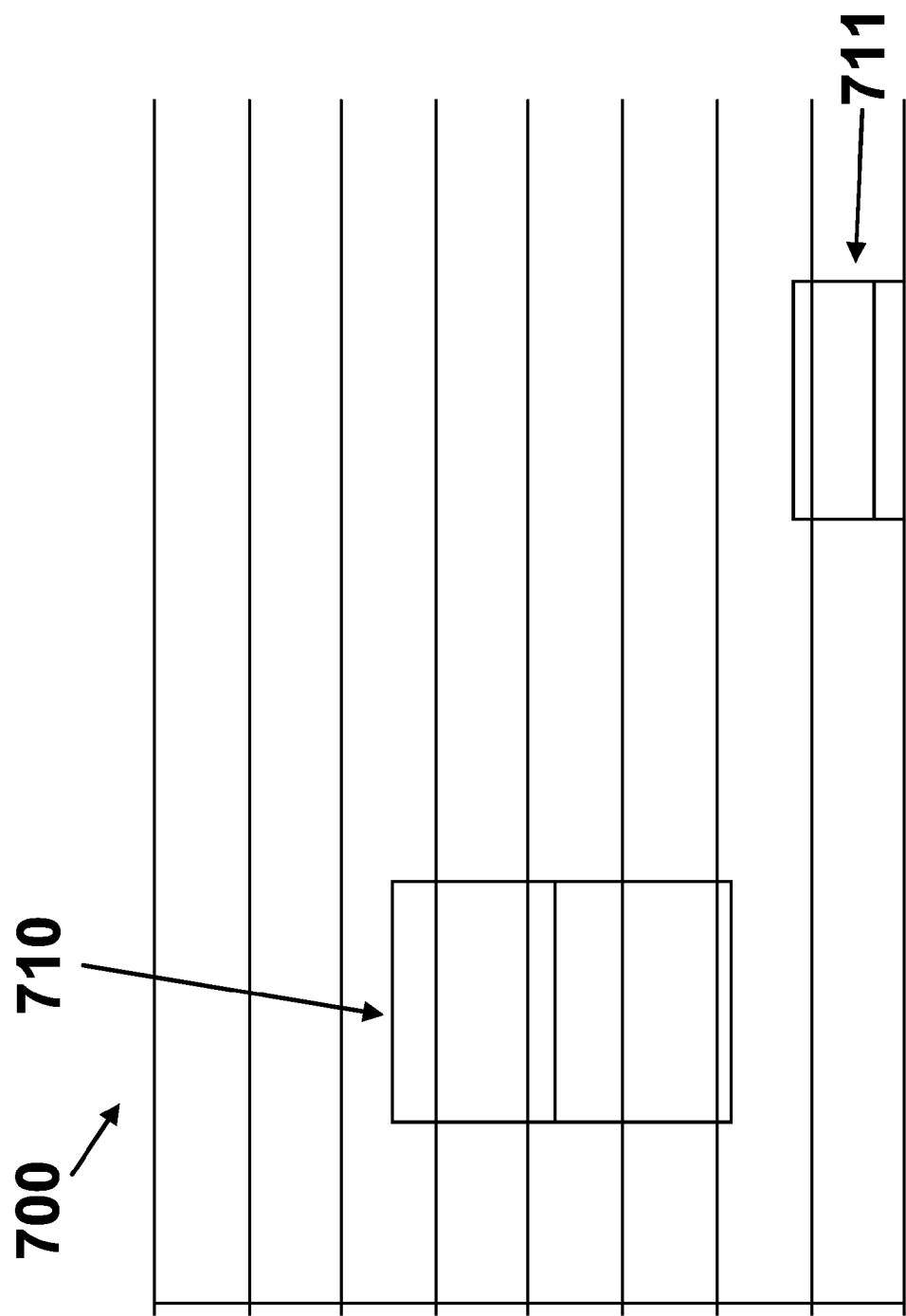
FIG. 12 is depicting results from an exemplary experiment of an auto-sensing configuration.

The results of the measurement are presented in FIG. 12 in a box plot 700. A clear improvement of the accuracy and the variation of the measured values are obtained when the laser and detector are moved into the package and the distance is measured compared to if the package is placed between the laser and detector with a fixed distance.

FIG. 12 demonstrating the improved performance of gas sensing as the laser and detector are moved into close distance to the package walls and the distance is measured ('distance adjustment') 711 compared to fixed positioned light source head and detector head ('No adjustment') 710. The sample oxygen content of the container was 0.6% O2.

Example of Headspace Gas Analysis of Tray Package

In an example, the headspace gas in tray packages was analysed. Tray packages with MAP consist of a rigid plastic tray that may be transparent or coloured. To protect the food contents, the tray is filled with a gas mixture and a plastic film is sealed around the edges of the tray. The plastic film is typically transparent or partially transparent. Often, the tray is filled with a slight overpressure so that the top film bulges upward. The bulging is typically not well defined, so there is a need to create a well-defined optical path length in the headspace in order to analyze the gas inside.

Figure 13A:
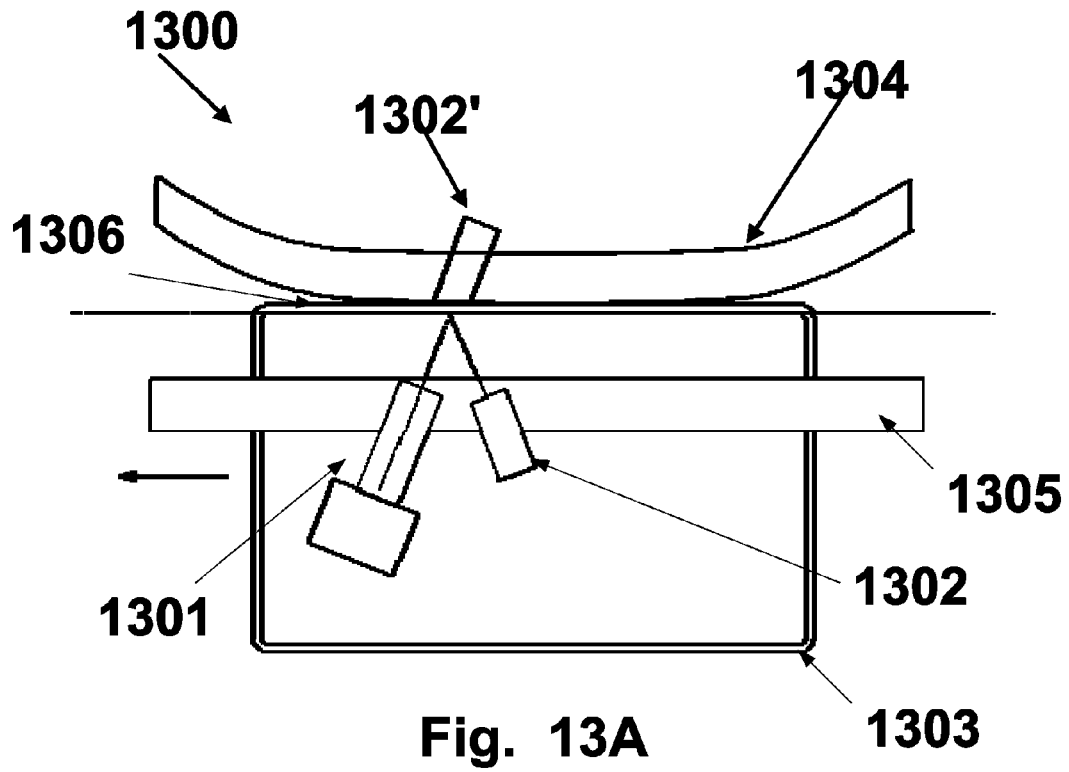
FIGS. 13 A and B are illustrating an exemplary gas measurement configuration where a light beam is directed through a top of the tray and at a sidewall of the tray at an angle.
Figure 13B:
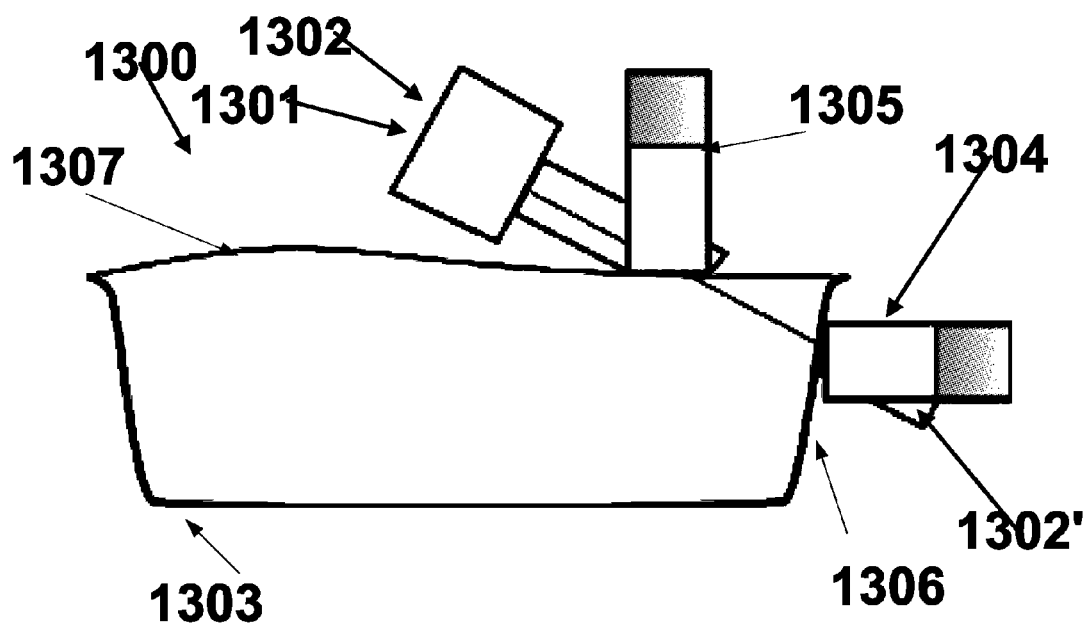

A gas measurement configuration is illustrated in FIGS. 13A and 13B. The illustrated configuration 1300 works similarly to the exemplary device described in relation to FIGS. 2 and 3.

FIG. 13A illustrates a configuration 1300 comprising a light source 1301, a detector in reflection configuration 1302. Alternatively, a detector in direct transmission configuration 1302' may be used. The sample is a tray 1303 (package) with a flexible protection 1307 being at least partly transparent, such as a film. The configuration further comprises a mechanical means 1305 for pushing down the protective top 1307, such as a foil, of the tray 1303. This mechanical mean 1305 is a means for making contact between an exterior of the walls or sides of the container and thereby creating a determinable optical path length through the container when contact is made. The configuration 1300 may also, in some examples, comprise a second mechanical means for positioning the tray 1305.

FIG. 13B illustrates the same exemplary configuration as illustrated in FIG. 13A but from a side view. Light source 1301 and detector 1302 in reflection configuration. The detector 1302' illiterates an alternative configuration in transmission mode. In FIGS. 13A and 13B, a light beam is directed at an angle by a light source 1301 through a top film 1307 of the tray 1303 and through a headspace at the sidewall 1306 of the tray 1303. This configuration ensures that the contents of the package may not interfere with the light beam. Depending on whether the sidewall 1306 of the tray 1303 is transparent or not, either a detector in reflection mode 1302 or a detector in transmission mode 1302' may be used. Alternatively, in the case the sidewall 1306 of the tray 1303 is transparent; a reflecting surface could be used instead of the detector 1302' (not illustrated).

In the illustrated example, the tray 1303 is positioned aided by an optional mechanical device 1304 so that the position of the sidewall is well defined. The assembly 1305 pushes down the top of the film 1307 to provide a well-defined optical path inside the headspace between the laser 1301 and the sidewall 1306. Thereby creating a well-defined optical path length between the laser 1301 and the detector 1302, 1302'.

In some examples, the light source 1301 and detector 1302 are mechanically mounted on the mechanical device 1305.

Figure 14:
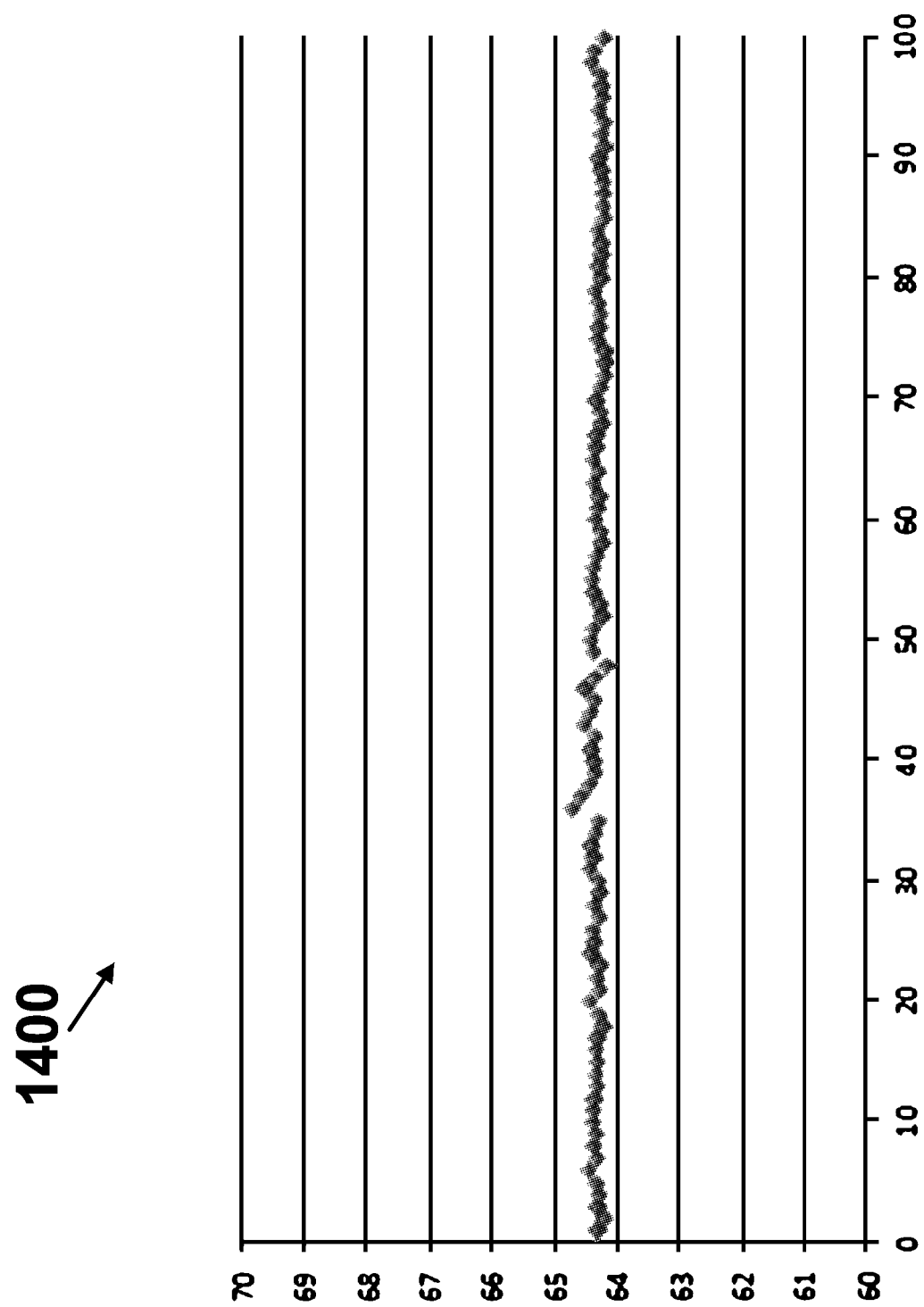
FIG. 14 is illustrating results from exemplary O2 measurements on a tray.

FIG. 14 presents 100 actual measurements 1400 of O2 concentration in percent in a tray using the described setup in relation to FIGS. 13A and 13B. The tray had black sidewalls and transparent top film. The tray was filled with minced meat. Even though the tray was made of black plastic, there was sufficient diffuse reflection from the sidewall to provide a useful signal. While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Also, different method steps than those described above, performing the method by hardware, may be provided within the scope of the disclosure. The different features and steps of the disclosure may be combined in other combinations than those described. The scope of the disclosure is only limited by the appended patent claims.

The invention claimed is:

1. A method of determining a concentration of a gas in a container having at least one flexible or variable side or wall, said method comprising:
   creating an optical path length through said container having a shape by modifying said shape of said container for creating said optical path length by inflating at least a portion of said container;
   transmitting a light signal between a light source head and a detector head through said optical path length being said inflated portion of said container;
   determining said concentration of said gas in said container based on detected light and said determinable optical path length.

2. The method of claim 1, comprising modifying said shape of said container for said creating said created optical path length through said container having a shape.

3. The method of claim 1, comprising positioning a light source head and a detector head against at least one of said at least one flexible or variable side or wall.

4. The method of claim 3, wherein said modifying said shape of said container includes pulling at least one side or wall a distance relative at least one second side or wall by using at least one movable temporary attachment point, thereby creating said determinable optical path length through said container.

5. The method of claim 1, comprising:
   moving one movable temporary attachment point towards said container;
   temporarily attaching at least one wall or side to said movable temporary attachment point, thereby creating said optical path length through said container.

6. The method of claim 1, comprising modifying said shape of said container by pushing at least one side or wall a distance towards at least one second side or wall at one location thereby inflating the container at a second location creating said optical path length through said container at said second location.

7. The method of claim 1, comprising
   moving said light source head and/or detector head towards at least one wall or side of said container;
   detecting when said light source head and detector head is in contact with said walls or sides of said container, thereby creating said optical path length through said container; or
   moving either said light source head or detector head towards at least one wall or side of said container; and
   detecting when said moved light source head or detector head is in contact with said walls or sides of said container, thereby creating said optical path length through said container.

8. The method of claim 3, wherein modifying said shape of said container comprising:
   positioning said container in an enclosure having walls;
   at least partly evacuating an atmosphere of said enclosure and thereby expanding said container so that said walls or sides of said container make contact with said walls of said enclosure thereby creating said optical path length through said container.

9. The method of claim 1, comprising positioning said light source head and said detector head at opposite sides of said optical path length; or positioning said light source head and said detector head at the same side of said optical path length and a reflective means at an opposite side.

10. The method of claim 1, comprising utilizing a calibration routine based on using two laser beams, instead of determining said optical path length.

11. The method of claim 1, comprising a calibration routine based on measurements on a second container having an equal optical path length and a known concentration of said gas.

12. The method of claim 1, wherein said container is a tray with a flexible protection layer, such as a film, being at least partly transparent and wherein the method comprises pushing down said flexible protection layer by a mechanical means and a light signal is transmitted at an angle by said light source through said flexible protection layer of said tray and through a headspace and at a sidewall of said tray, detecting signal a reflected by said sidewall or transmitted through said sidewall.

13. A system for measuring a concentration of a gas in a container having at least one flexible or variable side or wall, said system comprises:
a light source head and a detector head;
a contact mechanism disposed adjacent to and outside of said container; said contact mechanism applying force to said container, thereby expanding or inflating at least a portion of said container to create an optical path length through the expanded or inflated portion;
a control unit determining said concentration of a gas in said container based on detected light sent through said optical path length and said created optical path length.

14. The system of claim 13, wherein said contact mechanism is at least one movable temporary attachment point having an attachment mechanism that engages an exterior of said walls or sides of said container and pulls said at least one flexible or variable side or wall of said container a distance relative at least a second side or wall to create said optical path length through said container.

15. The system of claim 13, wherein said contact mechanism is mechanical fixtures configured for pushing at a first location on said at least one flexible or variable side or wall of said container a distance towards at least a second side or wall at one first location thereby inflating said container at a second location creating said optical path length through said container at said second location upon said pushing.

16. The system of claim 13, wherein said contact mechanism is movable to position said light source head and detector head in contact with at least one wall or side of said container;
said contact mechanism comprising a sensor for detecting when said light source head and/or detector head is in contact with at least one wall or side of said container, thereby creating said optical path length through said container, or
said contact mechanism being movable to position said light source head or detector head in contact with said at least one wall or side of said container; and
said contact mechanism comprising a sensor for detecting when said moved light source head or detector head is in contact with at least one wall or side of said container, thereby creating said optical path length through said container.

17. The system of claim 13, wherein said contact mechanism is an enclosure configured for said container to be positioned in;
said contact mechanism comprising a unit for at least partly evacuating an atmosphere of said enclosure wherein said container is expanded so that said walls or sides of said container can make contact with said walls of said enclosure, thereby creating said optical path length through said container upon said at least partly evacuation of said atmosphere.

18. The system of claim 13, wherein said light source head and said detector head are arranged at opposite sides of said optical path length; or said light source head and said detector head are arranged at the same side of said optical path length and a reflective means at an opposite side of said container.

19. The system of claim 13, wherein said container is a tray with a flexible protection layer being at least partly transparent and wherein said contact mechanism pushes downward said flexible protection layer such that said light signal is transmitted at an angle by said light source through said flexible protection layer of said tray and through a headspace and at a sidewall of said tray, said signal is reflected by or transmitted through said sidewall of said tray and is detected by said detector.

* * * * *